US012698350B2

(12) United States Patent
Gebhardt et al.

(10) Patent No.: US 12,698,350 B2
(45) Date of Patent: Aug. 4, 2026

(54) PHOTOPOLYMERIZABLE DENTAL COMPOSITES WITH RAPID CURING AND LOW SHRINKAGE STRESS

(71) Applicant: Ivoclar Vivadent AG, Schaan (LI)

(72) Inventors: Benjamin Gebhardt, Grabs (CH); Norbert Moszner, Triesen (LI)

(73) Assignee: Ivoclar Vivadent AG, Schaan (LI)

( * ) Notice: Subject to any disclaimer, the term of this patent is extended or adjusted under 35 U.S.C. 154(b) by 614 days.

(21) Appl. No.: 18/310,802

(22) Filed: May 2, 2023

(65) Prior Publication Data

US 2023/0265220 A1 Aug. 24, 2023

Related U.S. Application Data

(63) Continuation-in-part of application No. 16/653,119, filed on Oct. 15, 2019.

(30) Foreign Application Priority Data

Oct. 15, 2019 (EP) .................................... 18208916

(51) Int. Cl.

| | |
|---|---|
| ***C08F 2/48*** | (2006.01) |
| ***A61K 6/62*** | (2020.01) |
| ***A61K 6/76*** | (2020.01) |
| ***C08F 2/44*** | (2006.01) |
| ***C08F 20/10*** | (2006.01) |
| ***C08F 228/02*** | (2006.01) |

(52) U.S. Cl.

CPC .................. *C08F 2/48* (2013.01); *A61K 6/62* (2020.01); *A61K 6/76* (2020.01); *C08F 2/44* (2013.01); *C08F 20/10* (2013.01); *C08F 228/02* (2013.01)

(58) Field of Classification Search

None

See application file for complete search history.

(56) References Cited

U.S. PATENT DOCUMENTS

| | | | | |
|---|---|---|---|---|
| 9,532,929 | B2 * | 1/2017 | Fornof | A61K 6/60 |
| 9,758,478 | B2 * | 9/2017 | Fornof | C08F 290/067 |
| 10,342,744 | B2 * | 7/2019 | Moszner | A61K 6/62 |
| 11,673,980 | B2 * | 6/2023 | Gebhardt | C08F 20/18 523/116 |
| 2002/0076549 | A1 * | 6/2002 | Welch | C08F 290/062 359/581 |
| 2012/0295228 | A1 * | 11/2012 | Abuelyaman | C07C 323/12 977/773 |
| 2017/0156993 | A1 * | 6/2017 | Moszner | A61K 6/62 |
| 2018/0142082 | A1 * | 5/2018 | Liska | C08K 5/42 |
| 2018/0369075 | A1 * | 12/2018 | Moszner | A61K 6/887 |

OTHER PUBLICATIONS

Braga, R. et al., Factors involved in the development of polymerization shrinkage stress in resin-composites: A systematic review, Dental Materials, 2005, vol. 21, pp. 962-970.

Gorsche, C. et al., Exploring the benefits of Beta-allyl sulfones for more homogeneous dimethacrylate photopolymer networks, Journal of Polymer Chemistry, 2015, vol. 6, pp. 2038-2047.

Gorsche, C. et al., Rapid formation of regulated methacrylate networks yielding tough materials for lithography-based 3D printing, Journal of Polymer Chemistry, 2016, vol. 7, pp. 2009-2014.

Seidler, K. et al., Vinyl Sulfonate Esters: Efficient Chain Transfer Agents for the 3D Printing of Tough Photopolymers without Retardation, Angew. Chem. Int. Ed., 2018, vol. 57, pp. 9165-9169.

Stansbury, J.W., Dimethacrylate network formation and polymer property evolution as determined by the selection of monomers and curing conditions, Dental Materials, 2012, vol. 28, pp. 13-22.

* cited by examiner

*Primary Examiner* — Peter A Salamon

(74) *Attorney, Agent, or Firm* — Ann M. Knab; Thad McMurray

(57) ABSTRACT

Radically polymerizable material, which contains (a) 0.01 to 5 wt.-% of at least one transfer reagent, (b) 5 to 60 wt.-% of at least one multifunctional (meth)acrylate or a mixture of mono- and multifunctional (meth)acrylates, (c) 0.01 to 3.0 wt.-% of a mixture of at least one monomolecular and at least one bimolecular photoinitiator, (d) 30 to 90 wt.-% of at least one filler, and (e) optionally additive(s), wherein the material contains as transfer reagent (a) at least one allyl sulfone of Formula I and/or a vinyl sulfone ester of Formula II.

27 Claims, No Drawings

PHOTOPOLYMERIZABLE DENTAL COMPOSITES WITH RAPID CURING AND LOW SHRINKAGE STRESS

CROSS-REFERENCE TO RELATED APPLICATIONS

This application is a continuation-in-part application of and claims priority to U.S. application Ser. No. 16/653,119, filed on Oct. 15, 2019, which claims priority to European patent application No. 18208916.9 filed on Nov. 28, 2018, all the disclosures of which are incorporated herein by reference in their entirety.

TECHNICAL FIELD

The present invention relates to light-curing radically polymerizable materials, which are suitable in particular as dental filling composites, cements for inlays, onlays, crowns or bridges and as veneering materials.

BACKGROUND

Dental composites which are used e.g. as composite cement or as direct filling material for the production of inlays, onlays, crowns or as veneering material contain a polymerizable organic matrix and one or more fillers, which are usually surface-modified with a polymerizable bonding agent. Depending on the type of the fillers, the monomer matrix and the application the filler content can vary between 30 and 90 wt.-%, wherein cements have a lower filler content compared with filling composites. The polymerizable organic matrix is also referred to as resin.

As a rule, the polymerizable organic matrix contains a mixture of monomers, initiator components, stabilizers and pigments. Mixtures of dimethacrylates are usually used as resins. Examples of these are the high-viscosity dimethacrylates 2,2-bis[4-(2-hydroxy-3-methacryloyloxypropyl)phenyl]propane (bis-GMA) and 1,6-bis-[2-methacryloyloxyethoxycarbonylamino]-2,4,4-trimethylhexane (UDMA) or the lower-viscosity dimethacrylates, used as diluting monomers, bismethacryloyloxymethyltri-cyclo[5.2.1.]decane (TCDMA), decanediol-1,10-dimethacrylate ($D_3MA$) and triethylene glycol dimethacrylate (TEGDMA).

In the radical polymerization of dental composites the polymerization shrinkage ($\Delta V_P$) of the monomers used results in a volume contraction, which can lead to the very disadvantageous marginal gap formation in the case of tooth fillings.

During the polymerization of monofunctional methacrylates, such as e.g. methyl methacrylate (MMA) ($\Delta V_P$=21.0 vol.-%), the polymerization shrinkage does not lead to the build-up of a polymerization shrinkage force (PSF) as the reduction in the volume can be compensated for by a simple flow of the macromolecules formed. In the case of the crosslinking polymerization of multifunctional methacrylates, however, a three-dimensional polymer network already forms within a few seconds at the so-called gel point, i.e. already at a low monomer conversion, as a result of which the polymerization shrinkage can no longer be compensated for by viscous flow and the material builds up a considerable PSF as the monomer conversion increases. This leads to stresses and, in some cases, also to cracks in the material or to lifting off from the substrate. The development of the PSF or of corresponding stresses in filling composites is dependent on several further factors, including on the extent of the volume contraction during polymerization (curing or post-curing), the viscoelastic properties (modulus of elasticity and modular structure), the glass transition temperature ($T_G$) of the polymer, the viscosity and the flow behaviour, the polymerization kinetics, the polymer network formation (resin functionality, crosslinking density, proportion of cyclic structures, polymerization rate, temperature, monomer and double-bond conversion), the type of curing and the type of restoration (layer thickness, cavity geometry). A particularly high shrinkage stress is observed in the case of light curing (cf. R. R. Braga, R. Y. Ballester, J. L. Ferracane, Dent. Mater. 21 (2005) 962-970; J. W. Stansbury, Dent. Mater. 28 (2012) 13-22).

Numerous strategies have been pursued to reduce the PSF. This includes clinical methods, such as e.g. the incremental layer technique, the use of cavity varnishes with a low modulus of elasticity to form a stress-absorbing layer or the preheating of the composites to improve the flow properties. The use of monomers with ring-opening polymerizable groups or the use of crosslinking agents with photo- or thermolabile spacers can likewise lead to composites with a low PSF.

In addition, it has been attempted to reduce the PSF through the addition of hyperbranched monomers, nanogels or nanotubes as well as low-profile additives or expandable fillers.

US 2012/0295228 A1, which is hereby incorporated by reference, discloses radically polymerizable dental materials which contain ethylenically unsaturated monomers with disulfide groups, which are effective as addition-fragmentation materials and which are intended to reduce the PSF.

WO 2015/057413 A1 and corresponding US 20160229800 (A1) and U.S. Pat. No. 9,758,478 (B2), which US published application and patent are hereby incorporated by reference, disclose addition-fragmentation oligomers which contain disulfide groups in allyl positions. These can be added to radically polymerizable materials, wherein the labile bonds can be cleaved and reformed during the polymerization. The PSF is to be reduced thereby.

WO 2015/041863 A1 and corresponding US20160206520 (A1) and U.S. Pat. No. 9,532,929, which US published application and patent are hereby incorporated by reference, disclose crosslinking addition-fragmentation oligomers which contain trithiocarbonate structures. The oligomers can be added to radically polymerizable materials. They bring about a crosslinking of the materials, wherein the crosslinks are labile and can be cleaved and reformed during the polymerization. The PSF is to be reduced in this way.

A disadvantage is that the described composites with low shrinkage stress according to the state of the art cure relatively slowly and accordingly require a relatively long exposure time for curing.

SUMMARY

The object of the invention is to provide polymerizable dental materials which require a short exposure time for curing and which, after curing, have mechanical properties suitable for dental applications and in particular a low polymerization shrinkage force (PSF).

DETAILED DESCRIPTION

The object is achieved according to the invention by radically polymerizable materials, which contain (a) 0.01 to 5 wt.-% of at least one transfer reagent, (b) 5 to 60 wt.-% of at least one multifunctional (meth) acrylate or of a mixture of mono- and multifunctional (meth)acrylates, (c) 0.01 to 3.0 wt.-% of a combination of at least one monomolecular and at least one bimolecular photoinitiator, (d) 30 to 90 wt.-% of at least one filler, and (e) optionally additive(s), wherein the at least one monomolecular photoinitiator comprises a monoacylphosphine oxide, preferably a diacyldialkylgermanium compound, a tetraacylgermanium compound or a mixture thereof.

The material contains as transfer reagent (a) at least one allyl sulfone of Formula I Formula I

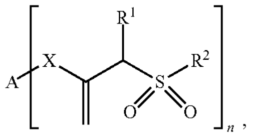

in which the variables have the following meanings:

A H; —CN; a phenyl radical, which can bear one or more substituents, such as $—CH_3$, $—C_2H_5$, —OH, $—OCH_3$, $—O—COCH_3$, a polymerizable vinyl, (meth)acryloyloxy or (meth)acrylamide group, or an aliphatic linear or branched $C_1$-$C_{20}$ alkylene or $C_1$-$C_{20}$ alkyl radical, which can be interrupted by one or more 1,4-phenylene groups, urethane groups, O or S, which can bear one or more substituents, such as —OH or $—OCH_3$, and which can bear a tri-$C_1$-$C_4$ alkoxysilyl group or a polymerizable vinyl, (meth)acryloyloxy or (meth)acrylamide group terminally;

$R^1$ in each case independently of one another H, an aliphatic linear or branched $C_1$-$C_9$ alkyl radical, tolyl or phenyl;

$R^2$ in each case independently of one another a phenyl radical, which can bear one or more substituents, such as $—CH_3$, $—C_2H_5$, —OH, $—OCH_3$, $—O—COCH_3$, a polymerizable vinyl, (meth)acryloyloxy or (meth)acrylamide group, $—C(═CH_2)—COOR^3$ or $—C(═CH_2)—CO—NR^4R^5$; or an aliphatic linear or branched $C_1$-$C_{20}$ alkyl radical, which can be interrupted by O or S and which can bear a polymerizable vinyl, (meth)acryloyloxy or (meth)acrylamide group, $—C(═CH_2)—COOR^3$ or $—C(═CH_2)—CO—NR^4R^5$ terminally, wherein $R^{3-5}$ independently of one another are in each case a linear or branched $C_{1-6}$ alkyl radical;

X —COO—, $—CON(R^6)—$ or is absent, wherein the bonding to A is effected via O or N and wherein $R^6$ is H; or an aliphatic linear or branched $C_1$-$C_{20}$ alkyl radical, which can be interrupted by one or more O or S and which can bear a polymerizable vinyl, (meth) acryloyloxy or (meth)acrylamide group, $—C(═CH_2)—COOR^3$ or $—C(═CH_2)—CO—NR^4R^5$ terminally, wherein $R^{3-5}$ independently of one another are in each case a linear or branched $C_{1-6}$ alkyl radical;

n an integer from 1 to 6, and/or a vinyl sulfone ester of Formula II

Formula II

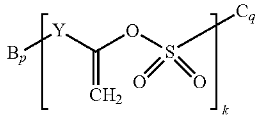

in which the variables have the following meanings:

B H, CN, a cycloaliphatic, linear or branched aliphatic $C_1$-$C_{30}$ hydrocarbon radical, which can be substituted by one or more, preferably 1 to 6, particularly preferably 1 to 3 substituents, preferably $—CH_3$, $—C_2H_5$, —OH, $—OCH_3$ and/or $—O—COCH_3$, which can be interrupted by one or more, preferably 1 to 4, particularly preferably 1 to 2 urethane groups, ester groups, O and/or S and which can contain 1 to 4, preferably 1 or 2 benzene groups, an aromatic $C_6$-$C_{30}$ hydrocarbon radical, which can be substituted by one or more, preferably 1 to 6, particularly preferably 1 to 3 substituents, preferably $—CH_3$, $—C_2H_5$, —OH, $—OCH_3$ and/or $—O—COCH_3$, or a combination thereof;

Y —COO—, $—CON(R^7)—$ or is absent, wherein the bonding to B is effected via O or N;

C a cycloaliphatic, linear or branched aliphatic $C_1$-$C_{30}$ hydrocarbon radical, which can be substituted by one or more, preferably 1 to 6, particularly preferably 1 to 3 substituents, preferably $C_1$-$C_5$ alkyl, —OH, $—O—COCH_3$ and/or $C_1$-$C_5$ alkoxy, which can be interrupted by one or more, preferably 1 to 4, particularly preferably 1 to 2 urethane groups, ester groups, O and/or S and which can contain 1 to 4, preferably 1 or 2 benzene groups, an aromatic $C_6$-$C_{30}$ hydrocarbon radical, which can be substituted by one or more, preferably 1 to 6, particularly preferably 1 to 3 substituents, preferably vinyl, $C_1$-$C_5$ alkyl, —OH, $—O—COCH_3$ and/or $C_1$-$C_5$ alkoxy, or tosyl, or a combination thereof;

$R^7$ hydrogen, a cycloaliphatic, linear or branched aliphatic $C_1$-$C_{10}$ hydrocarbon radical, which can be interrupted by one or more, preferably 1 to 4, particularly preferably 1 to 2 oxygen atoms and which can be substituted by one or more, preferably 1 to 4, particularly preferably 1 to 2 OH groups, or an aromatic $C_6$-$C_{10}$ hydrocarbon radical, which can be substituted by one or more, preferably 1 to 4, particularly preferably 1 to 2 OH groups;

p an integer from 1 to 6;

k an integer from 1 to 6;

q an integer from 1 to 6; wherein p and q cannot be greater than 1 at the same time and wherein if p=1, q=k, and if q=1, p=k.

Compounds of Formula I in which the variables have the following meanings are preferred:

A H; an aliphatic linear or branched $C_1$-$C_{14}$ alkylene or $C_1$-$C_{14}$ alkyl radical, which can be interrupted by one or more O or S, which can bear one or more substituents, such as —OH or $—OCH_3$, and which can bear a tri-$C_1$-$C_3$ alkoxysilyl group or a polymerizable vinyl, (meth)acryloyloxy or (meth)acrylamide group terminally;

$R^1$ H, an aliphatic branched or preferably linear $C_1$-$C_4$ alkyl radical, tolyl or phenyl;

$R^2$ in each case independently of one another a phenyl radical, which can bear one or more substituents, such as —$CH_3$, —$C_2H_5$, —OH, —$OCH_3$, —O—$COCH_3$; or an aliphatic linear or branched $C_1$-$C_{10}$ alkyl radical, which can be interrupted by O or S;

X —COO—, —CON($R^6$)— or is absent, wherein the bonding to A is effected via O or N and wherein $R^6$ is H; or an aliphatic linear or branched $C_1$-$C_{10}$ alkyl radical, which can be interrupted by one or more O or S;

n an integer from 1 to 3.

Compounds of Formula I in which the variables have the following meanings are particularly preferred:

A H; an aliphatic linear or branched $C_1$-$C_{12}$ alkylene or $C_1$-$C_{12}$ alkyl radical, which can be interrupted by one or more O and which can bear a tri-$C_1$-$C_2$ alkoxysilyl group or a polymerizable (meth)acryloyloxy group terminally;

$R^1$ H or an aliphatic linear $C_1$-$C_4$ alkyl radical;

$R^2$ in each case independently of one another a phenyl radical, which can bear one or more substituents, such as —$CH_3$, —$C_2H_5$, —OH, —$OCH_3$; or an aliphatic linear $C_1$-$C_6$ alkyl radical, which can be interrupted by O;

X —COO—, —CON($R^6$)— or is absent, wherein the bonding to A is effected via O or N and wherein $R^6$ is H; or an aliphatic linear $C_1$-$C_4$ alkyl radical;

n an integer from 1 to 2.

Compounds of Formula II in which the variables have the following meanings are preferred:

B H, a cycloaliphatic, linear or branched aliphatic $C_1$-$C_{15}$ hydrocarbon radical, which can be substituted by 1 to 4, particularly preferably 1 to 3 substituents, preferably —$CH_3$, —$C_2H_5$, —OH, —$OCH_3$ and/or —O—$COCH_3$, which can be interrupted by 1 to 4, particularly preferably 1 to 2 urethane groups, ester groups, O and/or S and which can contain 1 or 2 benzene groups, an aromatic $C_6$-$C_{18}$ hydrocarbon radical, which can be substituted by 1 to 6, particularly preferably 1 to 3 substituents, preferably —$CH_3$, —$C_2H_5$, —OH, —$OCH_3$ and/or —O—$COCH_3$, or a combination thereof;

Y —COO—, —CON($R^7$)— or is absent, wherein the bonding to B is effected via O or N;

C a cycloaliphatic, linear or branched aliphatic $C_1$-$C_{15}$ hydrocarbon radical, which can be substituted by 1 to 4, particularly preferably 1 to 3 substituents, preferably $C_1$-$C_4$ alkyl, —OH, —O—$COCH_3$ and/or $C_1$-$C_4$ alkoxy, which can be interrupted by 1 to 4, particularly preferably 1 to 2 urethane groups, ester groups, O and/or S and which can contain 1 or 2 benzene groups, an aromatic $C_6$-$C_{18}$ hydrocarbon radical, which can be substituted by 1 to 6, particularly preferably 1 to 3 substituents, preferably vinyl, $C_1$-$C_4$ alkyl, —OH, —O—$COCH_3$ and/or $C_1$-$C_4$ alkoxy, or tosyl, or a combination thereof;

$R^7$ hydrogen, a cycloaliphatic, linear or branched aliphatic $C_1$-$C_6$ hydrocarbon radical, which can be interrupted by one or more, preferably 1 to 2 oxygen atoms and which can be substituted by one or more, preferably 1 to 2 OH groups, or an aromatic $C_6$-$C_{10}$ hydrocarbon radical, which can be substituted by one or more, preferably 1 to 2 OH groups;

p an integer from 1 to 3;

k an integer from 1 to 3;

q an integer from 1 to 3; wherein p and q cannot be greater than 1 at the same time and wherein if p=1, q=k, and if q=1, p=k.

Compounds of Formula II in which the variables have the following meanings are particularly preferred:

B H, a cycloaliphatic, linear or branched aliphatic $C_1$-$C_{10}$ hydrocarbon radical, which can be substituted by 1 to 3 substituents, preferably —$CH_3$, —OH and/or —$OCH_3$, and which can be interrupted by 1 to 2 O, an aromatic $C_6$-$C_{10}$ hydrocarbon radical, which can be substituted by 1 to 3 substituents, preferably —$CH_3$, —OH and/or —$OCH_3$, or a combination thereof;

Y —COO—, wherein the bonding to B is effected via O;

C a cycloaliphatic, linear or branched aliphatic $C_1$-$C_{10}$ hydrocarbon radical, which can be substituted by 1 to 3 substituents, preferably $C_1$-$C_3$ alkyl, —OH, —O—$COCH_3$ and/or $C_1$-$C_3$ alkoxy, which can be interrupted by 1 to 2 O and/or S and which can contain 1 or 2 benzene groups, an aromatic $C_6$-$C_{10}$ hydrocarbon radical, which can be substituted by 1 to 3 substituents, preferably vinyl, $C_1$ to $C_3$ alkyl, —OH, —O—$COCH_3$ and/or $C_1$ to $C_3$ alkoxy, or tosyl, or a combination thereof;

p an integer from 1 to 2;

k an integer from 1 to 2;

q an integer from 1 to 2; wherein p and q cannot be greater than 1 at the same time and wherein if p=1, q=k, and if q=1, p=k.

The formulae extend only to those compounds which are compatible with the theory of chemical valence. For example, if A is hydrogen, n can only be 1, and if B is a $C_1$ radical, p can at most be 4. The indication that a radical is interrupted by one or more urethane groups, O atoms, S atoms etc. is to be understood to mean that these groups are in each case inserted into the carbon chain of the radical. These groups are thus bordered on both sides by C atoms and cannot be terminal. $C_1$ radicals cannot be interrupted. The indication that a radical contains a benzene group means, in contrast, that this group can also be terminal, wherein any remaining yl-positions are saturated by H. By combinations is meant groups which are composed of the meanings given in each case, for example of aromatic and aliphatic radicals, such as e.g. -Ph-$CH_2$-Ph-, or of several aromatic radicals, such as e.g. -Ph-Ph-, or of aromatic and/or aliphatic radicals and others of the named groups, such as e.g. -Ph-O-Ph- (Ph=phenyl).

Suitable allyl sulfones of Formula I and the preparation thereof are described in EP 2 965 741 A1. Particularly suitable allyl sulfones of Formula I are 2-(toluene-4-sulfonylmethyl)-acrylic acid ethyl ester (TSMEA), 2-(toluene-4-sulfonylmethyl)-acrylic acid 2-(2-ethoxyethoxy)-ethyl ester, 2-(toluene-4-sulfonylmethyl)-acrylic acid, 2-(toluene-4-sulfonylmethyl)-acrylic acid tert-butyl ester, 3-(trimethoxysilyl)propyl-2-(tosylmethyl) acrylate, 3-(triethoxysilyl)propyl-2-(tosylmethyl) acrylate, 3-(triethoxysilyl)propyl-2-(tosylmethyl)acrylamide, 2-(methylsulfonylmethyl)-ethyl acrylate, 2-(methylsulfonylmethyl)-propyl acrylate, triethylene glycol bis[2-(toluene-4-sulfonylmethyl) acrylate], 2-(toluene-4-sulfonylmethyl)-acrylic acid (2-methacryloyloxyethyl) ester, 2-(toluene-4-sulfonylmethyl)-acrylic acid (6-methacryloyloxyhexyl) ester, 2 -(toluene-4-sulfonylmethyl)-acrylic acid (10-methacryloyloxydecyl) ester, 2-(toluene-4-sulfonylmethyl)-acrylic acid (2-hydroxy-3-methacryloyloxypropyl) ester and 2-(toluene-4-sulfonylmethyl)- acrylic acid (8-methacryloyloxy-3,6-dioxaoctyl) ester, wherein 2-(toluene-4-sulfonylmethyl)-acrylic acid ethyl ester (TSMEA) is quite particularly suitable:

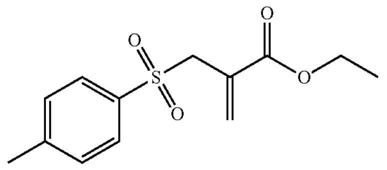

TSMEA

Suitable vinyl sulfone esters of Formula II and the preparation thereof are described in EP 3 090 772 A1. Particularly suitable vinyl sulfone esters of Formula II are 2-(toluene-4-sulfonyloxy)-acrylic acid ethyl ester (TSVEA), 2-methanesulfonyloxyacrylic acid ethyl ester, triethylene glycol bis[2-(toluene-4-sulfonyloxy) acrylate], 2-(2,4,6-triisopropyl-benzenesulfonyloxyacrylic acid octyl ester, 2-(toluene-4-sulfonyloxy)-acrylic acid 2-(tetrahydropyran-2-yloxy)-ethyl ester, 2-(toluene-4-sulfonyloxy)-acrylic acid 2-hydroxyethyl ester, 2-(toluene-4-sulfonyloxy)-acrylic acid 2,4,6-trimethylphenyl ester, 2-(4-vinylbenzenesulfonyloxy)-acrylic acid ethyl ester, 2-(toluene-4-sulfonyloxy)-acrylic acid methoxymethyl ester, 2-(2,4,6-triisopropylbenzene-sulfonyloxy)-acrylic acid methoxymethyl ester, 2-(2,4,6-triisopropylbenzenesulfonyloxy)-acrylic acid and diethyl-2,2'-[(1,3-phenyldisulfonyl)bis(oxy)] diacrylate, wherein 2-(toluene-4-sulfonyloxy)-acrylic acid ethyl ester (TSVEA) is quite particularly suitable:

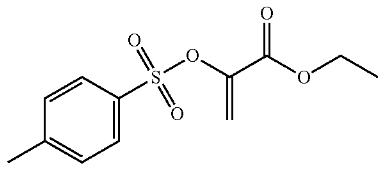

TSVEA

Materials which contain at least one multifunctional (meth)acrylate or a mixture of mono- and multifunctional (meth)acrylates as radically polymerizable monomer (b) are preferred according to the invention. By monofunctional (meth)acrylates is meant compounds with one, by multifunctional (meth)acrylates is meant compounds with two or more, preferably 2 to 4, radically polymerizable groups. The mono- or multifunctional (meth)acrylates can contain further functional groups, such as e.g. hydroxy, ester, silyl or ureido groups. The flexibility and the properties of the cured materials can be influenced in a targeted manner via the structure of the radically polymerizable (meth)acrylate comonomers. Thus, e.g., a higher proportion of multifunctional (meth)acrylates leads to a higher degree of crosslinking and thus to a material with lower flexibility. In contrast to this, the addition of e.g. monofunctional (meth)acrylates with flexible side chains leads to a higher flexibility. Functional groups contained in the (meth)acrylates, such as e.g. hydroxy groups, can increase the strength of the material through polar interactions.

Suitable mono- or multifunctional (meth)acrylates are 2-hydroxyethyl, benzyl, tetrahydrofurfuryl or isobornyl methacrylate, p-cumylphenoxyethylene glycol methacrylate (CMP-1E), bisphenol A dimethacrylate, bis-GMA (an addition product of methacrylic acid and bisphenol A diglycidyl ether), ethoxylated or propoxylated bisphenol A dimethacrylate, such as e.g. 2-[4-(2-(meth)acryloyloxyethoxyethoxy) phenyl]-2-[4-(2-methacryloyloxyethoxy)phenyl]propane) (SR-348c, from Sartomer; contains 3 ethoxy groups) or 2,2-bis[4-(2-methacryloxypropoxy)phenyl]propane (bis-PMA), UDMA (an addition product of 2-hydroxyethyl methacrylate and 2,2,4- or 2,4,4-trimethylhexamethylene-1,6-diisocyanate), di-, tri- or tetraethylene glycol dimethacrylate, trimethylolpropane trimethacrylate, pentaerythritol tetramethacrylate, as well as glycerol di- and trimethacrylate, bismethacryloyloxy-methyltricyclo[5.2.1.]decane (TCDMA), 1,4-butanediol di-methacrylate, 1,10-decanediol dimethacrylate ($D_3MA$), 1,12-dodecanediol dimethacrylate or mixtures thereof.

Bisphenol A dimethacrylate, bis-GMA (an addition product of methacrylic acid and bisphenol A diglycidyl ether), 2-[4-(2-(meth)acryloyloxyethoxyethoxy)phenyl]-2-[4-(2-methacryloyloxy-ethoxy)phenyl]propane) (SR-348c, Sartomer), 2,2-bis[4-(2-meth-acryloxypropoxy)phenyl]propane (bis-PMA), UDMA (an addition product of 2-hydroxyethyl methacrylate and 2,2,4- or 2,4,4-trimethylhexamethylene-1,6-diisocyanate), bismethacryloyloxy-methyltricyclo[5.2.1.] decane (TCDMA) and mixtures thereof are particularly suitable.

The named monomers are particularly suitable for the production of dental materials.

The materials according to the invention preferably contain no thermolabile radically polymerizable monomers, photolabile radically polymerizable monomers or a mixture thereof. By thermolabile and photolabile monomers are meant monomers containing groups that can be cleaved thermally or by irradiation, respectively, in particular the thermolabile and photolabile monomers according to US 2017/0156993 A1, which is incorporated herein by reference in its entirety.

The materials according to the invention preferably contain as photoinitiators (c) a combination of at least one monomolecular photoinitiator and at least one bimolecular photoinitiator, more preferably such photoinitiators which are active in a wavelength range of from 400 to 500 nm. The at least one monomolecular photoinitiator and the at least one bimolecular photoinitiator are preferably used in a ratio of from 2:1 to 1:2, relative to their proportions by weight. The at least one monomolecular photoinitiator and the at least one bimolecular photoinitiator are particularly preferably used in a ratio of from 1.4:1 to 1:2, relative to their proportions by weight. The at least one monomolecular photoinitiator and the at least one bimolecular photoinitiator are quite particularly preferably used in a ratio of from 1.2:1 to 1:1.8 and most preferably 1:1 to 1:1.8, relative to their proportions by weight.

According to one embodiment of the invention, the at least one monomolecular photoinitiator and the at least one bimolecular photoinitiator are used in a weight ratio of from 2:1 to 1.1:1, preferably in a weight ratio of from 1.7:1 to 1.2:1.

According to another embodiment of the invention, the at least one monomolecular photoinitiator and the at least one bimolecular photoinitiator are used in a weight ratio of from 1:1.1 to 1:2, preferably in a weight ratio of from 1:1.2 to 1:1.7.

Preferred monomolecular photoinitiators are monoacylphosphine oxides, and more preferably diacyldialkylgermanium and tetraacylgermanium compounds as well as tetraacylstannanes. Particularly preferred monomolecular photoinitiators are 2,4,6 -trimethylbenzoyl diphenylphosphine oxide, and in particular dibenzoyldiethylgermane, bis(4-methoxybenzoyl)diethylgermanium (MBDEGe, Ivocerin®), tetrabenzoylgermane, tetrakis(o-methyl-benzoyl) germane, tetrakis(mesitoyl)stannane and mixtures thereof.

α-Diketones or derivatives thereof are preferably suitable as bimolecular photoinitiators. Particularly suitable α-diketones or derivatives thereof are camphorquinone (CQ), 9,10-phenanthrenequinone, 1-phenylpropane-1,2-dione, 2,2-dimethoxy-2-phenylacetophenone, diacetyl or 4,4'-dichlorobenzil or derivatives thereof. Camphorquinone (CQ), 2,2-dimethoxy-2-phenylacetophenone and mixtures thereof are quite particularly preferred. α-Diketones in combination with amines as reducing agent, such as e.g. 4-(dimethylamino)-benzoic acid ester (EDMAB), N,N-dimethylaminoethyl methacrylate, N,N-dimethyl-sym.-xylidine, triethanolamine and mixtures thereof, are most preferred. A ratio of bimolecular photoinitiator to amine of from 1:1 to 1:6, relative to their proportions by weight, is preferably used.

Particularly preferred combinations of at least one monomolecular photoinitiator, at least one bimolecular photoinitiator and at least one amine as reducing agent are mixtures of at least one of bis(4-methoxybenzoyl)diethylgermane (MBDEGe, Ivocerin®), tetrakis(o-methylbenzoyl)germane and tetrakis(mesitoyl)stannane as monomolecular photoinitiator; camphorquinone (CQ) and/or 2,2-dimethoxy-2-phenylacetophenone as bimolecular photoinitiator; and 4-(dimethylamino)benzoic acid ester (EDMAB) as reducing agent.

Quite particularly preferred combinations of a monomolecular photoinitiator, at least one bimolecular photoinitiator and an amine as reducing agent are mixtures of bis(4-methoxybenzoyl)diethylgermane (MBDEGe, Ivocerin®) as monomolecular photoinitiator; camphorquinone (CQ) and/or 2,2-dimethoxy-2-phenylacetophenone as bimolecular initiator; and 4-(dimethylamino)benzoic acid ester (EDMAB) as reducing agent. According to one embodiment, the materials according to present invention do not contain a bisacylphosphine oxide, with materials, which do not contain a monoacylphosphine oxide, bisacylphosphine oxide or a mixture thereof being preferred. More preferred are materials, which contain no monomolecular photoinitiators other than the at least one diacyldialkyl-germanium compound or tetraacylgermanium compound.

Preferred fillers (d) are inorganic particulate fillers, in particular oxides, such as $SiO_2$, $ZrO_2$ and $TiO_2$ or mixed oxides of $SiO_2$, $ZrO_2$, ZnO and/or $TiO_2$, nanoparticulate or microfine fillers, such as pyrogenic silica or precipitated silica, glass powders, such as quartz, glass ceramic or radiopaque glass powders, preferably barium or strontium aluminium silicate glasses, and radiopaque fillers, such as ytterbium trifluoride, tantalum(V) oxide, barium sulfate or mixed oxides of $SiO_2$ with ytterbium(III) oxide or tantalum (V) oxide. Furthermore, the dental materials according to the invention can contain fibrous fillers, nanofibres, whiskers or mixtures thereof.

Preferably the oxides, such as $SiO_2$, $ZrO_2$ and $TiO_2$ or mixed oxides of $SiO_2$, $ZrO_2$, ZnO and/or $TiO_2$, have a particle size of from 0.010 to 15 μm; the nanoparticulate or microfine fillers, such as pyrogenic silica or precipitated silica, have a particle size of from 10 to 300 nm; the glass powders, such as quartz, glass ceramic or radiopaque glass powders, preferably barium or strontium aluminium silicate glasses, have a particle size of from 0.01 to 15 μm, preferably of from 0.2 to 1.5 μm; and the radiopaque fillers, such as ytterbium trifluoride, tantalum(V) oxide, barium sulfate or mixed oxides of $SiO_2$ with ytterbium(III) oxide or tantalum(V) oxide, have a particle size of from 0.2 to 5 μm.

Particularly preferred fillers are mixed oxides of $SiO_2$ and $ZrO_2$ with a particle size of from 10 to 300 nm, glass powders with a particle size of from 0.2 to 1.5 μm, such as radiopaque glass powders of e.g. barium or strontium aluminium silicate glasses, and radiopaque fillers with a particle size of from 0.2 to 5 μm, such as ytterbium trifluoride, or mixed oxides of $SiO_2$ with ytterbium(III) oxide.

In addition, ground prepolymers (isofillers) consisting of polymer particles which preferably comprise radiopaque glass powder(s) and ytterbium trifluoride are suitable as filler.

Unless otherwise indicated, all particle sizes are weight-average particle sizes, in which the particle size in the range of from 0.1 μm to 1000 μm is determined by means of static light scattering, preferably using an LA-960 static laser scattering particle size analyzer (Horiba, Japan). Here, a laser diode with a wavelength of 655 nm and an LED with a wavelength of 405 nm are used as light sources in a measurement range of from 0.1 to 1000 μm. The use of two light sources with different wavelengths makes it possible to measure the entire particle size distribution of a sample in only one measurement pass, wherein the measurement is carried out as a wet measurement. For this a 0.1 to 0.5% aqueous dispersion of the filler is prepared and the scattered light thereof is measured in a flow-through cell. The scattered light analysis for the calculation of particle size and particle size distribution is effected according to the Mie theory in accordance with DIN/ISO 13320.

Particle sizes smaller than 0.1 μm are preferably determined by means of dynamic light scattering (DLS). The measurement of the particle size in the range of from 5 nm to 0.1 μm is preferably effected by dynamic light scattering (DLS) of aqueous particle dispersions, preferably using a Malvern Zetasizer Nano ZS (Malvern Instruments, Malvern UK) with an He—Ne laser with a wavelength of 633 nm, at a scattering angle of 90° at 25° C.

Particle sizes smaller than 0.1 μm can also be determined by means of SEM or TEM spectroscopy. Transmission electron microscopy (TEM) is preferably carried out with a Philips CM30 TEM at an accelerating voltage of 300 kV. For the preparation of the samples, drops of the particle dispersion are applied to a 50-Å-thick copper grid (mesh size 300), which is coated with carbon, and then the solvent is evaporated.

The light scattering decreases as the particle size decreases, however fillers with a small particle size have a greater thickening action. The fillers are subdivided into macrofillers and microfillers according to the particle size. Macrofillers are obtained by grinding quartz, radiopaque glasses, borosilicates or ceramic, are purely inorganic in nature and usually consist of splintery parts. Macrofillers with an average particle size of from 0.2 to 10 μm are preferred. Pyrogenic $SiO_2$ or precipitated silica or mixed oxides, e.g. $SiO_2$—$ZrO_2$, which are accessible by hydrolytic co-condensation of metal alkoxides (preferably used as microfiller). The microfillers preferably have an average particle size of from approx. 5 to 100 nm.

The fillers are preferably surface-modified, particularly preferably by silanization, quite particularly preferably by radically polymerizable silanes, in particular with 3-methacryloyloxypropyltrimethoxysilane. For the surface modification of non-silicate fillers, e.g. of $ZrO_2$ or $TiO_2$, functionalized acidic phosphates, such as e.g. 10-methacryloyloxydecyl dihydrogen phosphate, can also be used.

The materials according to the invention can optionally contain further additives, preferably stabilizers, colorants, microbiocidal active ingredients, fluoride-ion-releasing additives, blowing agents, optical brighteners, plasticizers or UV absorbers.

According to the invention it was found that through the combination of particular transfer reagents, radically polymerizable monomers and photoinitiators, materials can be obtained which cure after only a short exposure time. The materials according to the invention can be cured, for example, by exposure for 1 to 10 seconds with a radiance of from 1000 to 12,000 $mW/cm^2$, e.g. by exposure for 10 s with a radiance of from 1000 to 1400 $mW/cm^2$. The curing is preferably effected by exposure for 5 s with a radiance of from 1600 to 2400 $mW/cm^2$, quite particularly preferably by exposure for 1 s with a radiance of from 8000 to 12,000 $mW/cm^2$ and most preferably by exposure for 3 s with a radiance of from 2700 to 3500 $mW/cm^2$ or for 2 s with a radiance of from 4000 to 6000 $mW/cm^2$. The materials according to the invention have the advantage that, in spite of the short exposure time and the short curing time associated with it, only a low PSF builds up, such that fillings without marginal gaps result. The materials are therefore particularly suitable as dental composites.

The materials according to the invention preferably have the following composition:

(a) 0.1 to 5 wt.-%, preferably 0.1 to 3 wt.-%, and more preferably 0.1 to 0.9 wt.-% of at least one transfer reagent of Formula(e) I and/or II, (b) 8 to 50 wt.-%, preferably 10 to 40 wt.-% of at least one multifunctional (meth)acrylate or of a mixture of mono- and multifunctional (meth)acrylates, (c) 0.05 to 3.0 wt.-% and preferably 0.1 to 2.0 wt.-% of a mixture of at least one monomolecular and at least one bimolecular photoinitiator, wherein the at least one monomolecular photoinitiator and the at least one bimolecular photoinitiator are preferably used in a ratio of from 1.4:1 to 1:2, particularly preferably in a ratio of from 1.2:1 to 1:2, relative to their proportions by weight, (d) 40 to 90 wt.-% and preferably 50 to 85 wt.-% of at least one filler, and (e) 0 to 5 wt.-%, preferably 0 to 3 wt.-% and particularly preferably 0.2 to 3 wt.-% additive(s).

The materials according to the invention more preferably contain the following components:

(a) 0.1 to 5 wt.-%, preferably 0.1 to 3 wt.-%, and more preferably 0.1 to 0.9 wt.-% of at least one transfer reagent of Formula(e) I and/or II, (b) 10 to 40 wt.-% of at least one multifunctional (meth) acrylate selected from bisphenol A dimethacrylate, bis-GMA (an addition product of methacrylic acid and bisphenol A diglycidyl ether), 2-[4-(2-(meth)acryloyloxy-ethoxyethoxy)phenyl]-2-[4-(2-methacryloyloxy-ethoxy)phenyl]-propane) (SR-348c, Sartomer), 2,2-bis [4-(2-methacryl-oxypropoxy)phenyl]propane (bis-PMA), UDMA (an addition product of 2-hydroxyethyl methacrylate and 2,2,4- or 2,4,4-trimethylhexamethylene-1,6-diisocyanate), bismethacryloyl-oxymethyltricyclo[5.2.1.]decane (TCDMA) and mixtures thereof, (c) 0.1 to 2.0 wt.-% of a mixture of diacyldialkylgermanium, tetraacylgermanium and tetraacylstannane compounds or mono- or bisacylphosphine oxides with a bimolecular photoinitiator, preferably camphorquinone (CQ) and/or 2,2-dimethoxy-2-phenylacetophenone, as well as with 4-(dimethylamino)benzoic acid ester (EDMAB), wherein the at least one monomolecular photoinitiator and the at least one bimolecular photoinitiator are preferably used in a ratio of from 1.4:1 to 1:2, particularly preferably in a ratio of from 1.2:1 to 1:2, relative to their proportions by weight, (d) 50 to 85 wt.-% filler selected from mixed oxides of $SiO_2$, $ZrO_2$, glass powder, such as radiopaque glass powder of e.g. barium or strontium aluminium silicate glasses, and radiopaque fillers, such as ytterbium trifluoride, or mixed oxides of $SiO_2$ with ytterbium(III) oxide, ground prepolymers which contain a mixture of polymer particles as well as radiopaque glass powder(s) and ytterbium trifluoride, and mixtures thereof, and (e) 0.2 to 3 wt.-% additive(s).

Unless otherwise indicated, all percentages herein are in percent by weight and relate to the total mass of the material.

Materials which consist of the named substances are particularly preferred. Furthermore, those materials are preferred in which the individual components are in each case selected from the above-named preferred and particularly preferred substances.

The materials according to the invention also have mechanical properties, such as e.g. a high flexural strength, a high flexural modulus, a great hardness and a low shrinkage stress, which are advantageous for dental applications, in particular for prostheses or stereolithographically produced shaped bodies. They allow the production of prostheses and shaped bodies with high dimensional stability and high breaking strength.

An important advantage of the materials according to the invention is their lower shrinkage stress. After polymerization, the materials preferably have a shrinkage stress of from 60 to 110 N, particularly preferably of from 65 to 100 N and quite particularly preferably of from 70 to 90 N. The shrinkage stress can be determined e.g. with a Bioman shrinkage stress measurement device. For this, a defined quantity of the material is introduced into a gap between a metal cylinder, which is secured to a cantilever load-cell, and a glass plate and is then cured by exposure through the glass plate (1, 2, 3 and 10 s at 10,000, 5000, 3400 or 1200 $mW/cm^2$). The tension thereby applied to the cantilever load-cell is converted into an electrical signal using an amplified voltage indicator-energy converter and recorded. Using a calibration curve, the electrical signals are converted into the shrinkage stress in Newtons (N). The shrinkage stress in N is obtained by dividing the shrinkage stress by the contact surface area of the measuring cylinder.

The materials according to the invention furthermore have the advantage of a high flexural strength. After polymerization, the materials according to the invention preferably have a flexural strength of from 75 to 140 MPa, particularly preferably of from 80 to 135 MPa and quite particularly preferably of from 85 to 130 MPa. The flexural strength is determined in accordance with ISO Standard ISO-4049 (Dentistry—Polymer-based filling, restorative and luting materials).

In addition, the materials according to the invention are characterized by a high flexural modulus. After polymerization, the materials preferably have a flexural modulus of from 8.5 to 12.5 GPa, particularly preferably of from 9.0 to 12.0 GPa and quite particularly preferably of from 9.3 to 11.8 GPa. The flexural modulus of elasticity is determined in accordance with ISO Standard ISO-4049 (Dentistry—Polymer-based filling, restorative and luting materials).

A further advantage of the materials according to the invention is their great hardness. After polymerization, the materials preferably have a Vickers hardness of from 500 to 700 MPa, particularly preferably of from 500 to 670 MPa and quite particularly preferably of from 500 to 650 MPa. The Vickers hardness is tested at a depth of 4 mm by measuring the hardness profile (VH) in accordance with EN ISO 6507-1:2006-03. The Vickers hardness is preferably measured using a standardized hardness testing machine (ZHU0.2/Z2.5 model, from Zwick Roell, indenter: Vickers diamond pyramid (136°), variable hardness measuring head, test force range of from 2 to 200 Newtons).

The materials according to the invention are particularly suitable as dental filling materials, cements and veneering materials as well as as materials for the production of prostheses, artificial teeth, inlays, onlays, crowns and bridges.

The dental materials are suitable primarily for intraoral application by the dentist for the restoration of damaged teeth (clinical materials), i.e. for therapeutic application, e.g. as dental cements, filling composites and veneering materials. However, they can also be used extraorally, i.e. not therapeutically, for example in the production or repair of dental restorations, such as prostheses, artificial teeth, inlays, onlays, crowns and bridges (technical materials).

The materials according to the invention are also suitable for the production of shaped bodies for dental, but also for non-dental, purposes, e.g. by means of casting, compression moulding and in particular by additive processes such as 3D printing.

The invention is explained in more detail in the following with reference to examples.

EXAMPLES

Example 1

Preparation of Composites Based on Allyl or Vinyl Sulfone Esters

Composite pastes with the compositions according to Table 1 were prepared using a kneader. All composite pastes contained a mixture of bis-GMA, UDMA, SR-348c, bis-PMA and TCDMA. As photoinitiator mixture, they contained a monomolecular initiator (bis(4-methoxybenzoyl) diethylgermanium, Ivocerin®), a bimolecular initiator (camphorquinone (CQ)) and an amine as reducing agent (4-(dimethylamino)-benzoic acid ester (EDMAB)). Composite material B contained an allyl sulfone ester (TSMEA) as transfer reagent, material C contained a vinyl sulfone ester (TSVEA). Comparison material A contained no transfer reagent.

From the composite pastes, corresponding test pieces were prepared and, in each case, exposed using a polymerization lamp (Bluephase G4 (390-510 nm) with Power Cure (3 s) mode) for 10 s (1200 mW/cm$^2$), 3 s (3060 mW/cm$^2$), 2 s (5000 mW/cm$^2$) and 1 s (10,000 mW/cm$^2$), and thus cured. The flexural strength and the flexural modulus of elasticity were determined in accordance with ISO Standard ISO-4049 (Dentistry—Polymer-based filling, restorative and luting materials) (Table 2). The measurements were carried out after 24 h storage in water (37° C.).

The double-bond conversion (DBC) at a depth of 4 mm was determined by means of FTIR spectroscopy (Vertex 70 IR spectrometer, Bruker). In order to calculate the DBC, the peaks of the aliphatic (approx. 1650-1625 cm$^{-1}$) and aromatic (approx. 1620-1600 cm$^{-1}$) double bonds in the measured spectra were integrated and the ratio of the aliphatic to the aromatic double bonds was calculated from the previously determined integrals for each measured spectrum. Then, the average value (AV) of these ratios was calculated in each case for the ratios (R) of the unpolymerized samples and the polymerized samples. Finally, the values for the DBC were determined from the calculated average values in accordance with the following formula:

$$DBC[\%] = (1 - AV\ R_{polymerized} / AV\ R_{unpolymerized}) * 100.$$

The hardness at a depth of 4 mm was determined by means of Vickers hardness profile measurements (VH). The Vickers hardness was tested in accordance with EN ISO 6507-1:2006-03 using a standardized hardness testing machine (ZHU0.2/Z2.5 model, from Zwick Roell, indenter: Vickers diamond pyramid (136°), variable hardness measuring head, test force range of from 2 to 200 Newtons).

The shrinkage stress (SF) of the composites was determined using a Bioman shrinkage stress measuring device. For this, a defined quantity of composite of from 0.15 to 0.25 g was introduced into a gap between a metal cylinder, which is secured to a cantilever load-cell, and a glass plate and then irradiated through the glass plate using a dental exposure unit, and thereby polymerized. The tension forming on the cantilever load-cell was converted into an electrical signal using an amplified voltage indicator-energy converter and recorded. Using a calibration curve, the electrical signals were converted into the shrinkage stress in Newtons (N).

Compared with composites B (TSMEA) and C (TSVEA), composite A (without transfer reagent) has worse mechanical properties at exposure times below 10 s. However, in spite of the higher double-bond conversion, the values for the shrinkage force in the case of composites B and C turn out to be much lower compared with composite A.

TABLE 1

Composition of the composites

| Function | Component | Composite A* (wt.-%) | Composite B (wt.-%) | Composite C (wt.-%) |
|---|---|---|---|---|
| Monomer | Bis-GMA[a] | 10.0 | 9.1 | 9.1 |
| | UDMA[b] | 5.0 | 5.0 | 5.0 |
| | SR-348c[c] | 2.3 | 2.3 | 2.3 |
| | Bis-PMA[d] | 3.5 | 3.5 | 3.5 |
| | TCDMA[e] | 1 | 1 | 1 |
| Initiator | Ivocerin ®[f] | 0.03 | 0.03 | 0.03 |
| | Camphorquinone | 0.04 | 0.04 | 0.04 |
| | EDMAB[g] | 0.13 | 0.13 | 0.13 |
| Filler | Isofiller[h] | 18 | 18 | 18 |
| | Glass filler[i] | 43 | 43 | 43 |
| | $SiO_2$-$ZrO_2$ Spherosil[j] | 11 | 11 | 11 |
| | $YbF_3$[k] | 6 | 6 | 6 |
| Transfer reagent | TSVEA[l] | — | 0.9 | — |
| | TSMEA[m] | — | — | 0.9 |
| Total | | 100 | 100 | 100 |

*comparison example

[a]addition product of methacrylic acid and bisphenol A diglycidyl ether

[b]addition product of 2-hydroxyethyl methacrylate and 2,2,4- or 2,4,4-trimethylhexamethylene-1,6-diisocyanate

[c]2-[4-(2-(meth)acryloyloxyethoxyethoxy)phenyl]-2-[4-(2-methacryloyloxyethoxy)phenyl]propane)

[d]2,2-bis[4-(2-methacryloxypropoxy)phenyl]propane

[e]bismethacryloyloxymethyltricyclo[5.2.1.]decane

[f]bis(4-methoxybenzoyl)diethylgermanium

[g]4-(dimethylamino)-benzoic acid ester

[h]ground composite material based on bis-GMA[a], UDMA[b], 1,12-dodecanediol dimethacrylate ($D_3MA$), benzoyl peroxide,silanized Ba-Al borosilicate glass filler (average particle size 0.4 μm), ytterbium fluoride (average particle size 0.2 μm)

[i]silanized barium aluminium borosilicate glass powder(average particle size of 0.7 μm)

[j]silanized $SiO_2$-$ZrO_2$ mixed oxide (average particle size 1.2 μm)

[k]ytterbium fluoride (average particle size 0.2 μm)

[l]2-(toluene-4-sulfonyloxy)-acrylic acid ethyl ester

[m]2-(toluene-4-sulfonylmethyl)-acrylic acid ethyl ester

TABLE 2

| Physical properties of the composites | | | | |
|---|---|---|---|---|
| Property | Exposure time [s] | Composite A* | Composite B | Composite C |
| Flexural strength [MPa] | 1 | 105 ± 7 | 115 ± 9 | — |
| | 2 | — | 120 ± 6 | 114 ± 4 |
| | 3 | — | 115 ± 9 | 116 ± 5 |
| | 10 | 100 ± 10 | 119 ± 4 | 119 ± 13 |
| Flexural modulus [GPa] | 1 | 9.6 ± 0.5 | 11.3 ± 0.5 | — |
| | 2 | — | 11.2 ± 0.5 | 10.1 ± 0.6 |
| | 3 | — | 11.3 ± 0.5 | 9.8 ± 0.5 |
| | 10 | 9.8 ± 0.5 | 11.2 ± 0.4 | 10.4 ± 0.2 |
| Vickers hardness [MPa] | 1 | 635/545 | 650/580 | — |
| | 2 | — | 670/560 | 660/595 |
| | 3 | — | — | 623/587 |
| | 10 | 640/520 | 660/570 | 670/635 |
| DBC[a] [%] | 1 | 44 ± 3 | 49 ± 2 | — |
| | 2 | — | 53 ± 2 | 49 ± 1 |
| | 3 | — | 47 ± 2 | 45 ± 4 |
| | 10 | 42 ± 2 | 51 ± 2 | 46 ± 1 |
| SFb [N] | 1 | 85 ± 5 | 88 ± 9 | — |
| | 2 | — | 86 ± 3 | 78 ± 1 |
| | 3 | — | — | 78 ± 3 |
| | 10 | 98 ± 2 | 83 ± 3 | 71 ± 2 |

*comparison example
[a]double-bond conversion
[b]shrinkage stress

Example 2

Preparation of Composites with Different Transfer Reagent Contents

Using a kneader, composite pastes corresponding to composite B from Example 1 were prepared, wherein the quantity of vinyl sulfone ester (TSVEA) used was varied (Table 3). From the composite pastes, corresponding test pieces were prepared, exposed using a polymerization lamp (Bluephase G4 (390-510 nm) with Power Cure (3 s) mode) for 3 s (3060 mW/cm$^2$), and thus cured. The flexural strength and the flexural modulus of elasticity were then measured in accordance with ISO Standard ISO-4049 (Dentistry—Polymer-based filling, restorative and luting materials) (Table 4). The measurements were carried out after 24 h storage in water (37° C.). The double-bond conversion (DBC) at a depth of 4 mm was determined by means of FTIR spectroscopy and the depth of cure (DOC) in accordance with ISO 4094 (Table 4).

It can be seen in Table 4 that composite E, with 0.7% transfer reagent, has the best mechanical properties overall.

TABLE 3

| Composition of the composites | | | | |
|---|---|---|---|---|
| Component | Comp. D (wt.-%) | Comp. E (wt.-%) | Comp. B (wt.-%) | Comp. F (wt.-%) |
| Bis-GMA[a] | 9.55 | 9.3 | 9.1 | 8.65 |
| UDMA[b] | 5.0 | 5.0 | 5.0 | 5.0 |
| SR-348c[c] | 2.3 | 2.3 | 2.3 | 2.3 |
| Bis-PMA[d] | 3.5 | 3.5 | 3.5 | 3.5 |
| TCDMA[e] | 1 | 1 | 1 | 1 |
| Ivocerin ®[f] | 0.03 | 0.03 | 0.03 | 0.03 |
| Camphorquinone | 0.04 | 0.04 | 0.04 | 0.04 |
| EDMAB[g] | 0.13 | 0.13 | 0.13 | 0.13 |
| Isofiller[h] | 18 | 18 | 18 | 18 |

TABLE 3-continued

| Composition of the composites | | | | |
|---|---|---|---|---|
| Component | Comp. D (wt.-%) | Comp. E (wt.-%) | Comp. B (wt.-%) | Comp. F (wt.-%) |
| Glass filler[i] | 43 | 43 | 43 | 43 |
| $SiO_2$-$ZrO_2$ Spherosil[j] | 11 | 11 | 11 | 11 |
| $YbF_3$[k] | 6 | 6 | 6 | 6 |
| TSVEA[l] | 0.45 | 0.7 | 0.9 | 1.35 |
| Total | 100 | 100 | 100 | 100 |

The meanings of the indices a-l can be found in Table 1.

TABLE 4

| Physical properties of the composites | | | | |
|---|---|---|---|---|
| Property | Composite D | Composite E | Composite B | Composite F |
| Flexural strength [MPa] | 100 ± 13 | 122 ± 5 | 115 ± 9 | 111 ± 6 |
| Flexural modulus [GPa] | 10.6 ± 0.5 | 11.3 ± 0.4 | 11.3 ± 0.5 | 10.1 ± 0.6 |
| DBC[a] [%] | 50 ± 2 | 50 ± 1 | 47 ± 2 | 54 ± 2 |
| DOC[b] [mm] | 3.0 | 3.1 | 2.9 | 3.0 |

[a]double-bond conversion
[b]depth of cure

Example 3

Clinical Marginal Integrity of Class II Fillings

The clinical marginal integrity of placed class II fillings was investigated in human teeth using composites A, B and E. The restorations were placed in the self-etch mode in combination with a dental adhesive (Adhese Universal, from Ivoclar Vivadent AG). For this, in each case two class II cavities were prepared in extracted molars of the lower jaw (coronal-apical depth 4 mm, buccolingual extent 5 mm) and filled with an adhesive/composite combination. Starting at the enamel, the tooth surface to be treated was completely wetted with adhesive and the adhesive was rubbed in on the tooth surface to be treated for at least 20 seconds. Next, the adhesive was blown with oil- and water-free compressed air until a shiny, immobile film had formed. Thereafter, the adhesive was polymerized according to the manufacturer's instructions by irradiation with light and then the composites were introduced into the cavities in each case in one layer and polymerized by irradiation with light (10 s, 1200 mW/cm$^2$; 3 s, 3060 mW/cm$^2$; 2 s, 5000 mW/cm$^2$; or 1 s, 10,000 mW/cm$^2$). The filled teeth were then subjected to artificial ageing by means of thermocycling (10,000×5° C./55° C., for 30 s each). Next, replicas were made from epoxy resin (Stycast) by means of impression moulding. The marginal quality of the approximal region of the filling was assessed using a scanning electron microscope at 200× magnification by determining the percentage of intact margin in relation to the total margin.

It can be seen from Table 5 that composites B and E according to the invention gave much higher values for the marginal integrity than comparison material A.

TABLE 5

| Marginal integrity after TC and CS | | | | |
|---|---|---|---|---|
| Property | Exposure time [s] | Composite A* | Composite B | Composite E |
| % intact margin | 1 | 8.9 ± 10.8 | 70.8 ± 8.1 | — |
| | 2 | — | — | 76.3 ± 10.8 |
| | 3 | — | — | 68.9 ± 15.5 |
| | 10 | 18.8 ± 16.3 | — | 64.8 ± 12.1 |

*Comparison example

The invention claimed is:

1. A radically polymerizable material, comprising (a) 0.01 to 5 wt.-% of at least one transfer reagent, (b) 5 to 60 wt.-% of at least one multifunctional (meth) acrylate or of a mixture of mono- and multifunctional (meth)acrylates, (c) 0.01 to 3.0 wt.-% of a mixture of at least one monomolecular and at least one bimolecular photoinitiator, (d) 30 to 90 wt.-% of at least one filler, and (e) optionally additive(s), in each case relative to the total mass of the material, wherein the at least one monomolecular photoinitiator comprises a tetraacylgermanium compound, wherein the material comprises as transfer reagent (a) at least one allyl sulfone of Formula I Formula I

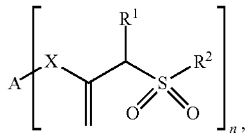

in which the variables have the following meanings:

A H; —CN; a phenyl radical, which can bear one or more substituents, such as $—CH_3$, $—C_2H_5$, —OH, $—OCH_3$, $—O—COCH_3$, a polymerizable vinyl, (meth)acryloyloxy or (meth)acrylamide group, or an aliphatic linear or branched $C_1$-$C_{20}$ alkylene or $C_1$-$C_{20}$ alkyl radical, which can be interrupted by one or more 1,4-phenylene groups, urethane groups, O or S, which can bear one or more substituents, such as —OH or $—OCH_3$, and which can bear a tri-$C_1$-$C_4$ alkoxysilyl group or a polymerizable vinyl, (meth)acryloyloxy or (meth)acrylamide group terminally;

$R^1$ in each case independently of one another H, an aliphatic linear or branched $C_1$-$C_9$ alkyl radical, tolyl or phenyl;

$R^2$ in each case independently of one another a phenyl radical, which can bear one or more substituents, such as $—CH_3$, $—C_2H_5$, —OH, $—OCH_3$, $—O—COCH_3$, a polymerizable vinyl, (meth)acryloyloxy or (meth)acrylamide group, $—C(=CH_2)—COOR^3$ or $—C(=CH_2)—CO—NR^4R^5$; or an aliphatic linear or branched $C_1$-$C_{20}$ alkyl radical, which can be interrupted by O or S and which can bear a polymerizable vinyl, (meth)acryloyloxy or (meth)acrylamide group, $—C(=CH_2)—COOR^3$ or $—C(=CH_2)—CO—NR^4R^5$ terminally, wherein $R^{3-5}$ independently of one another are in each case a linear or branched $C_{1-6}$ alkyl radical;

X —COO—, $—CON(R^6)—$ or is absent, wherein the bonding to A is effected via O or N and wherein $R^6$ is H; or an aliphatic linear or branched $C_1$-$C_{20}$ alkyl radical, which can be interrupted by one or more O or S and which can bear a polymerizable vinyl, (meth) acryloyloxy or (meth)acrylamide group, $—C(=CH_2)—COOR^3$ or $—C(=CH_2)—CO—NR^4R^5$ terminally, wherein $R^{3-5}$ independently of one another are in each case a linear or branched $C_{1-6}$ alkyl radical;

n an integer from 1 to 6, a vinyl sulfone ester of Formula II,

Formula II

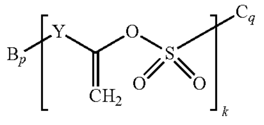

in which the variables have the following meanings:

B H, CN, a cycloaliphatic, linear or branched aliphatic $C_1$-$C_{30}$ hydrocarbon radical, which can be substituted by one or more substituents, which can be interrupted by one or more urethane groups, ester groups, O and/or S and which can contain 1 to 4 benzene groups, an aromatic $C_6$-$C_{30}$ hydrocarbon radical, which can be substituted by one or more substituents, or a combination thereof;

Y —COO—, $—CON(R^7)—$ or is absent, wherein the bonding to B is effected via O or N;

C a cycloaliphatic, linear or branched aliphatic $C_1$-$C_{30}$ hydrocarbon radical, which can be substituted by one or more substituents, which can be interrupted by one or more urethane groups, ester groups, O and/or S and which can contain 1 to 4 benzene groups, an aromatic $C_6$-$C_{30}$ hydrocarbon radical, which can be substituted by one or more substituents, or a combination thereof;

$R^7$ hydrogen, a cycloaliphatic, linear or branched aliphatic $C_1$-$C_{10}$ hydrocarbon radical, which can be interrupted by one or more oxygen atoms and which can be substituted by one or more OH groups, or an aromatic $C_6$-$C_{10}$ hydrocarbon radical, which can be substituted by one or more OH groups;

p an integer from 1 to 6;

k an integer from 1 to 6;

q an integer from 1 to 6; wherein p and q cannot be greater than 1 at the same time and wherein if p=1, q=k, and if q=1, p=k; and wherein the material does not contain a monoacylphosphine oxide, a bisacylphosphine oxide or a mixture thereof.

2. The material according to claim 1, in which the variables of Formula I have the following meanings:

A H; an aliphatic linear or branched $C_1$-$C_{14}$ alkylene or $C_1$-$C_{14}$ alkyl radical, which can be interrupted by one or more O or S, which can bear one or more substituents, such as —OH or $—OCH_3$, and which can bear a tri-$C_1$-$C_3$ alkoxysilyl group or a polymerizable vinyl, (meth)acryloyloxy or (meth)acrylamide group terminally;

$R^1$ H, an aliphatic branched or preferably linear $C_1$-$C_4$ alkyl radical, tolyl or phenyl;

$R^2$ in each case independently of one another a phenyl radical, which can bear one or more substituents, such as $—CH_3$, $—C_2H_5$, —OH, $—OCH_3$, $—O—COCH_3$; or an aliphatic linear or branched $C_1$-$C_{10}$ alkyl radical, which can be interrupted by O or S;

X —COO—, —CON($R^6$)— or is absent, wherein the bonding to A is effected via O or N and wherein $R^6$ H; or an aliphatic linear or branched $C_1$-$C_{10}$ alkyl radical, which can be interrupted by one or more O or S;

n an integer from 1 to 3, and/or in which the variables of Formula II have the following meanings:

B H, a cycloaliphatic, linear or branched aliphatic $C_1$-$C_{15}$ hydrocarbon radical, which can be substituted by 1 to 4 substituents comprising —$CH_3$, —$C_2H_5$, —OH, —$OCH_3$ and/or —O—$COCH_3$, which can be interrupted by 1 to 4 urethane groups, ester groups, O and/or S and which can contain 1 or 2 benzene groups, an aromatic $C_6$-$C_{18}$ hydrocarbon radical, which can be substituted by 1 to 6 substituents comprising-$CH_3$, —$C_2H_5$, —OH, —$OCH_3$ and/or —O—$COCH_3$, or a combination thereof;

Y —COO—, —CON($R^7$)— or is absent, wherein the bonding to B is effected via O or N;

C a cycloaliphatic, linear or branched aliphatic $C_1$-$C_{15}$ hydrocarbon radical, which can be substituted by 1 to 4 substituents comprising $C_1$-$C_4$ alkyl, —OH, —O—$COCH_3$ and/or $C_1$-$C_4$ alkoxy, which can be interrupted by 1 to 4 urethane groups, ester groups, O and/or S and which can contain 1 or 2 benzene groups, an aromatic $C_6$-$C_{18}$ hydrocarbon radical, which can be substituted by 1 to 6 substituents comprising vinyl, $C_1$-$C_4$ alkyl, —OH, —O—$COCH_3$ and/or $C_1$-$C_4$ alkoxy, or tosyl, or a combination thereof;

$R^7$ hydrogen, a cycloaliphatic, linear or branched aliphatic $C_1$-$C_6$ hydrocarbon radical, which can be interrupted by one or more oxygen atoms and which can be substituted by one or more OH groups, or an aromatic $C_6$-$C_{10}$ hydrocarbon radical, which can be substituted by one or more OH groups;

p an integer from 1 to 3;

k an integer from 1 to 3;

q an integer from 1 to 3; wherein p and q cannot be greater than 1 at the same time and wherein if p=1, q=k, and if q=1, p=k.

3. The material according to claim 2, wherein the at least one transfer reagent (a) according to Formula I is selected from 2-(toluene-4-sulfonylmethyl)-acrylic acid ethyl ester (TSMEA), 2-(toluene-4-sulfonylmethyl)-acrylic acid 2-(2-ethoxyethoxy)-ethyl ester, 2-(toluene-4-sulfonylmethyl)-acrylic acid, 2-(toluene-4-sulfonylmethyl)acrylic acid tert-butyl ester, 3-(trimethoxysilyl)propyl-2-(tosylmethyl) acrylate, 3-(triethoxysilyl)propyl-2-(tosylmethyl) acrylate, 3-(triethoxysilyl)propyl-2-(tosylmethyl)acrylamide, 2-(methylsulfonylmethyl)-ethyl acrylate, 2-(methylsulfonylmethyl)-propyl acrylate, triethylene glycol bis[2-(toluene-4-sulfonylmethyl) acrylate], 2-(toluene-4-sulfonylmethyl)-acrylic acid (2-methacryloyloxyethyl) ester, 2-(toluene-4-sulfonylmethyl)-acrylic acid (6-methacryloyloxyhexyl) ester, 2-(toluene-4-sulfonylmethyl)-acrylic acid (10-methacryloyloxydecyl) ester, 2-(toluene-4-sulfonylmethyl)-acrylic acid (2-hydroxy-3-methacryloyloxypropyl) ester, 2-(toluene-4-sulfonylmethyl)-acrylic acid (8-methacryloyloxy-3,6-dioxaoctyl) ester, and/or wherein the at least one transfer reagent (a) according to Formula II is selected from 2-(toluene-4-sulfonyloxy) acrylic acid ethyl ester (TSVEA), 2-methanesulfonyloxyacrylic acid ethyl ester, triethylene glycol bis[2-(toluene-4-sulfonyloxy) acrylate], 2-(2,4,6-triisopropyl-benzenesulfonyloxyacrylic acid octyl ester, 2-(toluene-4-sulfonyloxy)-acrylic acid 2-(tetrahydropyran-2-yloxy)-ethyl ester, 2-(toluene-4-sulfonyloxy)-acrylic acid 2-hydroxyethyl ester, 2-(toluene-4-sulfonyloxy)-acrylic acid 2,4,6-trimethylphenyl ester, 2-(4-vinylbenzenesulfonyloxy)-acrylic acid ethyl ester, 2-(toluene-4-sulfonyloxy)-acrylic acid methoxymethyl ester, 2-(2,4,6-triisopropylbenzenesulfonyloxy)-acrylic acid methoxymethyl ester, 2-(2,4,6-triisopropylbenzenesulfonyloxy)-acrylic acid or diethyl-2,2'-[(1,3-phenyldisulfonyl)bis(oxy)] diacrylate.

4. The material according to claim 1, comprising as component (b) at least one multifunctional (meth)acrylate selected from the group consisting of bisphenol A dimethacrylate, bis-GMA (an addition product of methacrylic acid and bisphenol A diglycidyl ether), 2-[4-(2-(meth)acryloyloxyethoxyethoxy)phenyl]-2-[4-(2-methacryloyloxyethoxy) phenyl]propane), 2,2-bis[4-(2-methacryloxypropoxy)phenyl]propane (bis-PMA), UDMA (an addition product of 2-hydroxyethyl methacrylate and 2,2,4- or 2,4,4-trimethylhexamethylene-1,6-diisocyanate) and bismuthacryloyloxymethyltricyclo[5.2.1.]decane (TCDMA).

5. The material according to claim 1, comprising as the at least one monomolecular photoinitiator a diacyldialkylgermanium or tetraacylgermanium compound, a monoacylphosphine oxide or a mixture thereof; and as the at least one bimolecular photoinitiator camphorquinone (CQ), 9,10-phenanthrenequinone, 1-phenylpropane-1,2-dione, 2,2-dimethoxy-2-phenylacetophenone, diacetyl, 4,4'-dichlorobenzil or a combination of camphorquinone (CQ), 9,10-phenanthrenequinone, 1-phenylpropane-1,2-dione, 2,2-dimethoxy-2-phenylacetophenone, diacetyl, 4,4'-dichlorobenzil with an amine selected from 4-(dimethylamino)-benzoic acid ester (EDMAB), N,N-dimethylaminoethyl methacrylate, N,N-dimethylsym-xylidine, triethanolamine or a mixture thereof.

6. The material according to claim 1, wherein the at least one monomolecular photoinitiator is bis(4-methoxybenzoyl) diethylgermane (MBDEGe); the at least one bimolecular photoinitiator is selected form a combination of camphorquinone (CQ), 2,2-dimethoxy-2-phenylacetophenone or a mixture thereof with the amine 4-(dimethylamino)-benzoic acid ester (EDMAB).

7. The material according to claim 1, in which the at least one monomolecular photoinitiator and the at least one bimolecular photoinitiator are used in a weight ratio of from 2:1 to 1:2.

8. The material according to claim 5, in which the bimolecular photoinitiator and the amine are used in a weight ratio of from 1:1 to 1:6.

9. The material according to claim 1, wherein the at least one filler (d) is selected from a mixed oxide of $SiO_2$ and $ZrO_2$, a glass powder comprising barium or strontium aluminium silicate glass powder, a radiopaque filler comprising ytterbium trifluoride or a mixed oxide of $SiO_2$ with ytterbium(III) oxide, a ground prepolymer or a mixture thereof.

10. The material according to claim 1, comprising (a) 0.1 to 5 wt.-% of the at least one transfer reagent of Formula(e) I and/or II, (b) 8 to 50 wt.-% of the at least one multifunctional (meth)acrylate or of the mixture of mono- and multi-functional (meth)acrylates, (c) 0.05 to 3.0 wt.-% of the mixture of at least one monomolecular and at least one bimolecular photoinitiator, (d) 40 to 90 wt.-% of the at least one filler, and (e) 0 to 5 wt.-% of the additive(s), in each case relative to the total mass of the material.

11. The material according to claim 10, comprising (a) 0.1 to 5 wt.-% of the at least one transfer reagent of Formula(e) I and/or II, (b) 10 to 40 wt.-% of at least one multifunctional (meth) acrylate selected from bisphenol A dimethacrylate, bis-GMA (an addition product of methacrylic acid and bisphenol A diglycidyl ether), 2-[4-(2-(meth)acryloyloxyethoxyethoxy)phenyl]-2-[4-(2-methacryloyloxyethoxy)phenyl]propane), 2,2-bis[4-(2-methacryloxypropoxy)phenyl]propane (bis-PMA), UDMA (an addition product of 2-hydroxyethyl methacrylate and 2,2,4- or 2,4,4-trimethylhexamethylene-1,6-diisocyanate), bismuthacryloyloxymethyltricyclo[5.2.1.]-decane (TCDMA) and mixtures thereof, (c) 0.1 to 2.0 wt.-% of a mixture of a diacyldialkylgermanium and/or tetraacylgermanium with a bimolecular photoinitiator selected from camphorquinone (CQ) and/or 2,2-dimethoxy-2-phenylacetophenone, or a combination of camphorquinone (CQ) and/or 2,2-dimethoxy-2-phenylacetophenone with 4-(dimethylamino)-benzoic acid ester (EDMAB), (d) 50 to 85 wt.-% filler selected from mixed oxides of $SiO_2$ and $ZrO_2$, glass powders, radiopaque fillers, mixed oxides of $SiO_2$ with ytterbium(III) oxide, ground prepolymers and mixtures thereof, and (e) 0.2 to 3 wt.-% additive(s), in each case relative to the total mass of the material.

12. The material according to claim 1 for intraoral use for the restoration of damaged teeth, or for intraoral use as dental cement, filling composite or veneering material.

13. A method of using the material according to claim 1 as material for the extraoral production or repair of dental restorations.

14. The method according to claim 13 for the production of artificial teeth, prostheses, inlays, onlays, crowns or bridges.

15. A method of using the material according to claim 1 for the production of shaped bodies by casting, compression moulding or 3D printing.

16. The material according to claim 1, which does not contain a bisacylphosphine oxide.

17. The material according to claim 1, which contains no monomolecular photoinitiators other than the at least one diacyldialkylgermanium compound or tetraacylgermanium compound.

18. The material according to claim 1, comprising 0.1 to 0.9 wt.-% of at least one transfer reagent (a).

19. The material according to claim 1, in which the at least one monomolecular photoinitiator and the at least one bimolecular photoinitiator are used in a weight ratio of from 2:1 to 1.1:1.

20. The material according to claim 1, in which the at least one monomolecular photoinitiator and the at least one bimolecular photoinitiator are used in a weight ratio of from 1.7:1 to 1.2:1.

21. The material according to claim 1, in which the at least one monomolecular photoinitiator and the at least one bimolecular photoinitiator are used in a weight ratio of from 1:1.1 to 1:2.

22. The material according to claim 1, in which the at least one monomolecular photoinitiator and the at least one bimolecular photoinitiator are used in a weight ratio of from 1:1.2 to 1:1.7.

23. The material according to claim 1, which does not contain a thermolabile radically polymerizable monomer, a photolabile radically polymerizable monomer or a mixture thereof.

24. The method of claim 13, comprising curing of the material by exposure for 1 to 10 seconds with a radiance of from 1000 to 12,000 $mW/cm^2$.

25. The method of claim 13, comprising curing of the material by exposure for 3 seconds with a radiance of from 2700 to 3500 $mW/cm^2$ or for 2 seconds with a radiance of from 4000 to 6000 $mW/cm^2$.

26. The method of claim 15, comprising curing of the material by exposure for 1 to 10 seconds with a radiance of from 1000 to 12,000 $mW/cm^2$.

27. The method of claim 15, comprising curing of the material by exposure for 3 seconds with a radiance of from 2700 to 3500 $mW/cm^2$ or for 2 seconds with a radiance of from 4000 to 6000 $mW/cm^2$.

* * * * *